United States Patent
Morimoto (10) Patent No.: US 10,073,030 B2
(45) Date of Patent: Sep. 11, 2018

(54) OPTICAL DETECTION DEVICE

(71) Applicant: KONICA MINOLTA, INC., Chiyoda-Ku, Tokyo (JP)

(72) Inventor: Takashi Morimoto, Suita (JP)

(73) Assignee: KONICA MINOLTA, INC., Tokyo (JP)

(*) Notice: Subject to any disclaimer, the term of this patent is extended or adjusted under 35 U.S.C. 154(b) by 0 days.

(21) Appl. No.: 15/532,492

(22) PCT Filed: Dec. 1, 2015

(86) PCT No.: PCT/JP2015/083681
§ 371 (c)(1),
(2) Date: Jun. 1, 2017

(87) PCT Pub. No.: WO2016/088733
PCT Pub. Date: Jun. 9, 2016

(65) Prior Publication Data
US 2017/0322150 A1    Nov. 9, 2017

(30) Foreign Application Priority Data
Dec. 1, 2014   (JP) .................................. 2014-243319

(51) Int. Cl.
| | |
|---|---|
| G01N 21/35 | (2014.01) |
| G01N 21/3504 | (2014.01) |
| G01M 3/38 | (2006.01) |
| G01N 33/00 | (2006.01) |
| G01N 21/27 | (2006.01) |
| G01N 21/17 | (2006.01) |

(52) U.S. Cl.
CPC .......... *G01N 21/3504* (2013.01); *G01M 3/38* (2013.01); *G01N 21/274* (2013.01); *G01N 33/0047* (2013.01); *G01N 2021/1765* (2013.01); *G01N 2021/3531* (2013.01)

(58) Field of Classification Search
CPC .......................... G01N 21/3504; G01N 21/274
See application file for complete search history.

(56) References Cited

U.S. PATENT DOCUMENTS

| | | | |
|---|---|---|---|
| 2005/0041840 A1* | 2/2005 | Lo ...................... | G06K 9/00288 382/118 |
| 2010/0133435 A1 | 6/2010 | Maillart et al. | |

FOREIGN PATENT DOCUMENTS

JP   2010522317 A   7/2010

OTHER PUBLICATIONS

International Search Report (ISR) and Written Opinion dated Feb. 16, 2016 issued in International Application No. PCT/JP2015/083681.

* cited by examiner

*Primary Examiner* — Casey Bryant
(74) *Attorney, Agent, or Firm* — Holtz, Holtz & Volek PC (57) ABSTRACT

In order to accurately detect a subject to be detected and reduce manufacturing or maintenance costs, this optical detection device determines whether there is a subject to be detected by determining a correction coefficient for correcting data from an image captured by a capturing sensor through a filter unit with an image data estimation value from when an image is captured without the filter unit, and comparing an image data estimation value obtained through correction using the correction coefficient from the image data with captured data obtained by capturing a detection area in a state where the filter unit is not in front of the capturing sensor.

20 Claims, 7 Drawing Sheets

OPTICAL DETECTION DEVICE

The present U.S. patent application is a U.S. National Phase application under 35 USC 371 of International Application No. PCT/JP2015/083681, filed Dec. 1, 2015. This application claims priority under the Paris Convention of Japanese patent Application No. 2014-243319, filed Dec. 1, 2014, the entirety of which is incorporated herein by reference.

TECHNICAL FIELD

The present invention relates to an optical detection device for detecting the presence or absence of a detection target object such as a gas in a space based on a shot image.

BACKGROUND ART

In factories, power plants, and the like, gasses are used in large quantities as chemical source materials and fuels. Gasses used as chemical source materials and fuels are often flammable or toxic, and their leaking outside may cause air pollution and fire and explosion accidents. Even with gasses with low toxicity, their presence at a high concentration may cause a low oxygen concentration, leading to asphyxiation and other accidents.

In facilities seen as factories and power plants where gasses are used, the piping and equipment through which gasses pass are checked carefully on a regular basis, and in addition gas leak detectors incorporating gas-sensitive elements are installed to watch for gas leaks. However, depending on the properties (such as specific gravity) of a gas and the current of air in a space, even if a plurality of gas leak sensors are installed, the gas may elude them and continue leaking, often resulting is inaccurate gas leak detection.

As a solution, there are proposed optical gas detection devices that utilize the optical absorption property peculiar to gasses. In an optical detection device, a space in which to detect a gas leak is shot with an image sensor; an increase or decrease under the influence of the gas in the black body radiation produced by an object constituting the background is detected, and thereby whether the gas is present or absent is determined. More specifically, image data in which the wavelengths influenced by the gas (for example, wavelengths absorbed or emitted by the gas) are cut with a filter or the like is shot with the image sensor. Then, with the filter replaced or removed, image data including the wavelengths influenced by the gas is shot with the image sensor. Then, the two sets of image data are compared with each other to detect a gas leak. Herein, radiated electromagnetic waves based on the temperature on the object surface is referred to as black body radiation.

Image sensors used in such optical gas detection devices divide into cooled sensors and uncooled sensors. Cooled sensors have the advantages of fast response and high sensitivity, but require a special cooling device. Thus, using a cooled sensor makes an optical gas detection device complicated and cumbersome.

By contrast, uncooled sensors require no cooling device, and thus using one helps make an optical gas detection device simple and compact. On the other hand, in an uncooled sensor, each pixel has a fine three-dimensional structure. This fine three-dimensional structure is prone to variations ascribable to the manufacturing process, and thus pixel characteristics are prone to variations. In an optical gas detection device employing art uncooled sensor, correction is performed to reduce variations in characteristics among the pixels of the uncooled sensor (see, for example, Ex-PCT Japanese Patent Application Publication No. 2010-522317).

In the remote optical gas detection device disclosed in Ex-PCT Japanese Patent Application Publication No. 2010-522317, a black body is arranged, the path of incoming light is obstructed with the black body (an infrared lens is obstructed), and an image sensor is corrected for heat drift; in this way, a shot image can be made uniform again. Thus, even when an uncooled sensor, which has lower accuracy than a cooled sensor, is used as an image sensor in an optical gas detection device, it is possible to detect a gas with high accuracy.

LIST OF CITATIONS

Patent Literature

Patent Document 1: Ex-PCT Japanese Patent Application Publication No 2010-522117

SUMMARY OF THE INVENTION

Technical Problem

The remote optical gas detection device disclosed in Ex-PCT Japanese Patent Application Publication No. 2010-522317 uses a black body for re-uniformizing of a shot image, and is provided with two driving mechanisms, namely one for moving the black body along the optical axis of the image sensor and one for driving a filter. Providing a plurality of driving mechanisms in this way makes the entire device large or complicated, requires higher manufacturing cost, and possibly restricts the installation site of the device. Moreover, the increased number of driving mechanisms leads to an increased failure rate and to increased maintenance and management work.

Against, the background described above, the present invention aims to provide an optical detection device that can detect a detection target object accurately and that helps reduce manufacturing and maintenance costs.

Means for Solving the Problem

To achieve the above aim, according to one aspect of the present invention, an optical detection device includes: an uncooled image sensor that has a plurality of pixels that convert light from a detection region into electricity; a filter that eliminates light in a wavelength range that is influenced by the detection target object; a filter driver that places or removes the filter in front of or from in front of the image sensor; and a processor that detects the presence or absence of the detection target by processing data from the image sensor. The processor determines a correction coefficient by which image data that is obtained by shooting through the filter is corrected to image data estimated values that are estimated to be obtained by shooting without the filter. The processor determines the presence or absence of the detection target object by comparing the image data estimated values that are obtained by correction using the correction coefficient from the image data with shot data that is obtained by shooting the detection region with the filter removed from in front of the image sensor.

Advantageous Effects of the Invention

According to the present invention, it is possible to provide an optical detection device that can detect a detection target object accurately and that helps reduce manufacturing and maintenance costs.

DESCRIPTION OF EMBODIMENTS

Embodiments of the present invention will be described below with reference to the accompanying drawings.

(First Embodiment)

Figure 1:
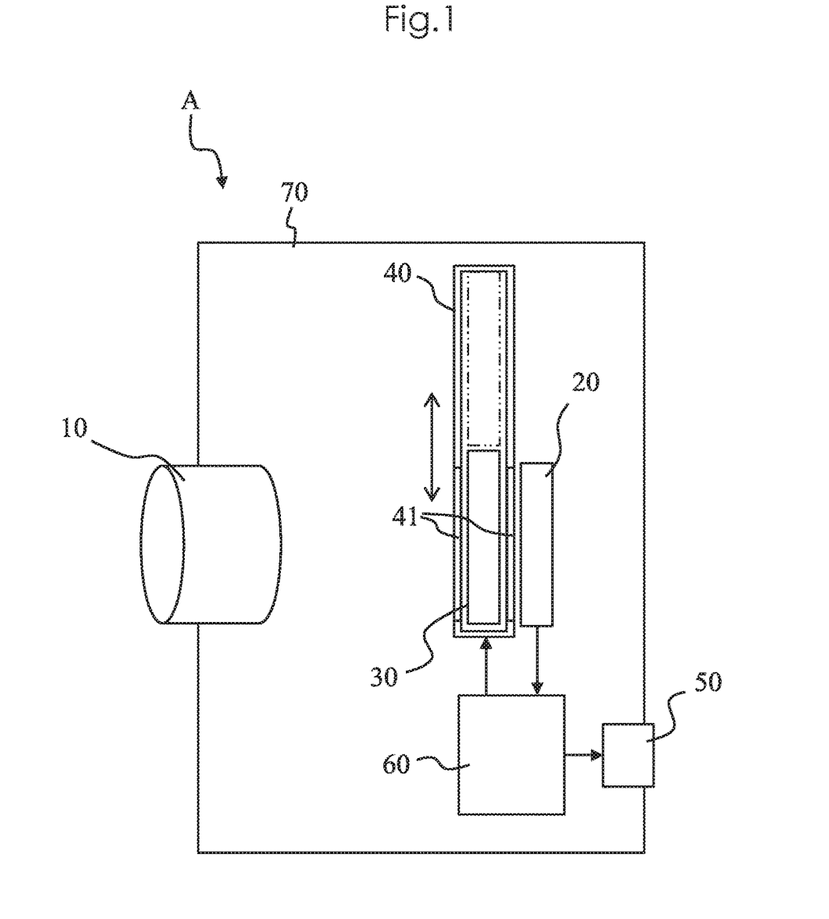
FIG. 1 is a schematic diagram of an optical detection device according to the present invention.

FIG. 1 is a schematic diagram of an optical detection device according to the present invention. The optical detection device A according to the present invention is a detection device that acquires an image of black body radiation light from a detection region to detect the presence or absence of a detection target object within the detection region. The detection target object absorbs, out of the black body radiation light (light in the infrared region), predetermined wavelengths. Thus, based on the image of the black body radiation light, change of the absorption wavelength of the detection target object is acquired, and the presence or absence of the detection target object within the detection region is detected. In this embodiment, examples of the detection target object detected by the optical detection device A include gasses in which gaseous chemical substances or particles are suspended (these will be collectively referred to as gaseous substances), though this is not meant as any limitation. For example, by a similar method, it is possible to detect liquid chemical substances mixed in water. In the following description, the term "optical" is not meant as any limitation to visible light, but is assumed to include also electromagnetic waves outside the visible region, such as infrared light and ultraviolet light.

As shown in FIG. 1, the optical detection device A includes an imaging optical system 10, an image sensor 20, a filter 30, a filter driver 40, a connection interface 50, and a processor 60. The optical detection device A has a housing 70, which forms its exterior.

The optical detection device A detects black body radiation light (light in the infrared region) from a detection region and, from change of the black body radiation light detected, detects the presence or absence of a detection target object. Accordingly, in the optical detection device A, the image sensor 20 detects black body radiation light (here, infrared light). The image sensor 20 has a configuration where photoelectric elements that receive infrared light and convert it into electricity are arrayed two-dimensionally. The image sensor 20 acquires an image of black body radiation by receiving, with those photoelectric elements, black body radiation light from the detection region. The image sensor 20 has a light reception surface at which it receives black body radiation light. In the following description, the photoelectric elements arrayed two-dimensionally are occasionally referred to also as pixels.

Figure 2:
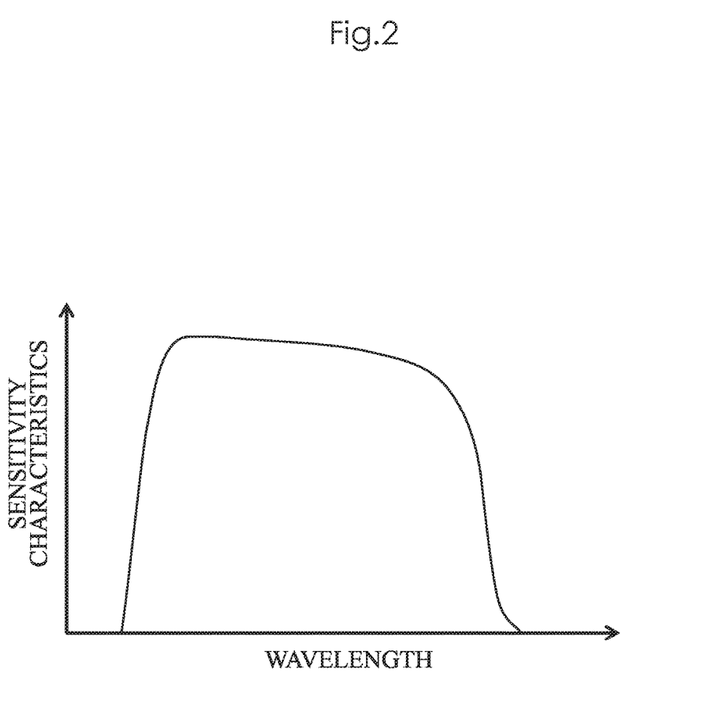
FIG. 2 is a graph showing spectroscopic sensitivity characteristics of an image sensor.

FIG. 2 is a graph showing the spectroscopic sensitivity characteristics of an image sensor. In the graph in FIG. 2, the vertical axis represents the sensitivity characteristics of the image sensor 20, and the horizontal axis represents wavelength. The image sensor 20 typically tends to have sensitivity characteristics as shown in FIG. 2. Specifically, the image sensor 20 has low sensitivity in a low wavelength range and a high wavelength range and high sensitivity in a medium wavelength range. Used as the image sensor 20 in the optical detection device A according to the present invention is one that has the region, in which it exhibits high sensitivity characteristics in the infrared region. The high-sensitivity wavelength range is determined according to the absorption wavelength of the detection target object to be detected, and it is preferable to select an image sensor 20 of which the high-sensitivity wavelength range includes the absorption wavelength of the detection target object.

The image sensor 20 is an uncooled sensor, of which examples include a microbolometer, a pyroelectric sensor, a diode sensor, and a thermopile sensor. For the image sensor 20, the wavelength range of the light (electromagnetic waves) that can be detected based on the absorption wavelength of the detection target object is determined, and an image sensor 20 that can detect light in that wavelength range is adopted. In the optical detection device A of this embodiment, a microbolometer is used as the image sensor 20.

The imaging optical system 10 is an optical system for imaging the black body radiation light from the detection region on the imaging surface of the image sensor 20. The imaging optical system 10 includes one or a plurality of lenses. The imaging optical system 10 is configured to change the angle of view of the imaging area, and to adjust focus, according to instructions from the processor 60. For the lens(es) used in the imaging optical system 10, a material that transmits the absorption wavelength of the detection target object is selected. For example, in a case where the absorption wavelength lies in a wavelength range spanning from the visible to near-infrared regions, an optical glass or the like is used; in a case where the absorption wavelength lies in a wavelength range spanning from the mid-infrared to far-infrared regions, an infrared light transmitting material such as Ge, Si, chalcogenide glass, or the like is used. For improved transmittance in a predetermined wavelength band, a coating is applied to the surface.

The filter 30 is arranged so as to be driven by the filter driver 40. The filter driver 40 is arranged between the imaging optical system 10 and the image sensor 20. The filter driver 40 has a transmissive portion 41 which transmits the light that is incident on the image sensor 20 from the imaging optical system 10. The filter driver 40 is configured to permit the filter 30 to reciprocate between a position where it covers the transmissive portion 41 and a position where its is retracted from the transmissive portion 41. Examples of the configuration of the filter driver 40 include one in which the filter 30 is arranged on a disc-form rotary member that is rotated and one that allows the filter 30 to reciprocate linearly. Examples of the driving source include a motor that produces a rotative force, a linear motor, and a solenoid.

Figure 3A:
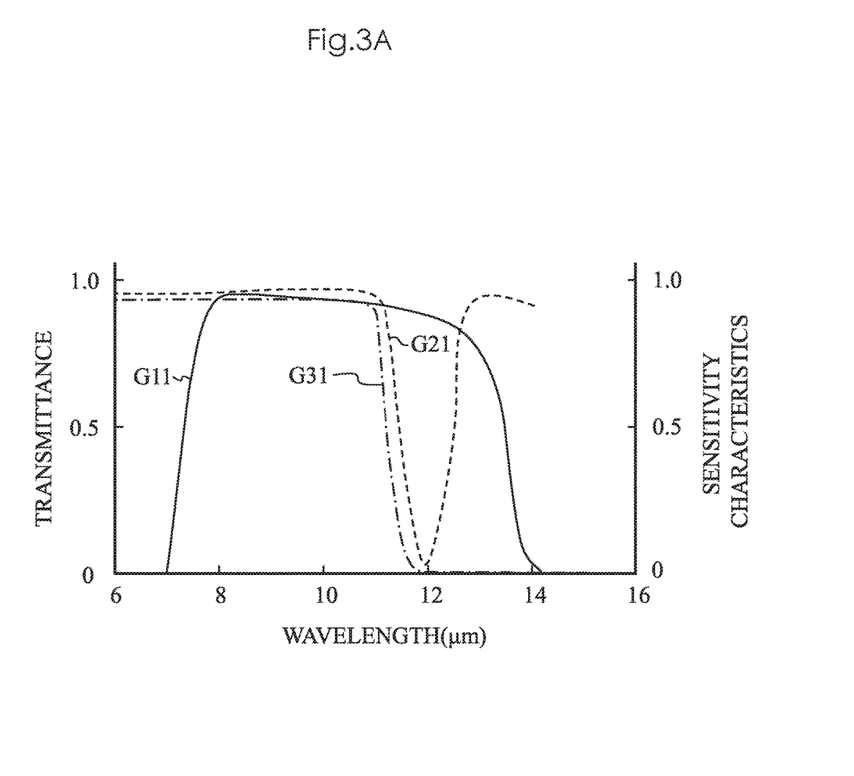
FIG. 3A is a graph showing spectroscopic transmittance characteristics of a detection target object, spectroscopic transmittance characteristics of a filter, and spectroscopic sensitivity characteristics of an image sensor.
Figure 3B:
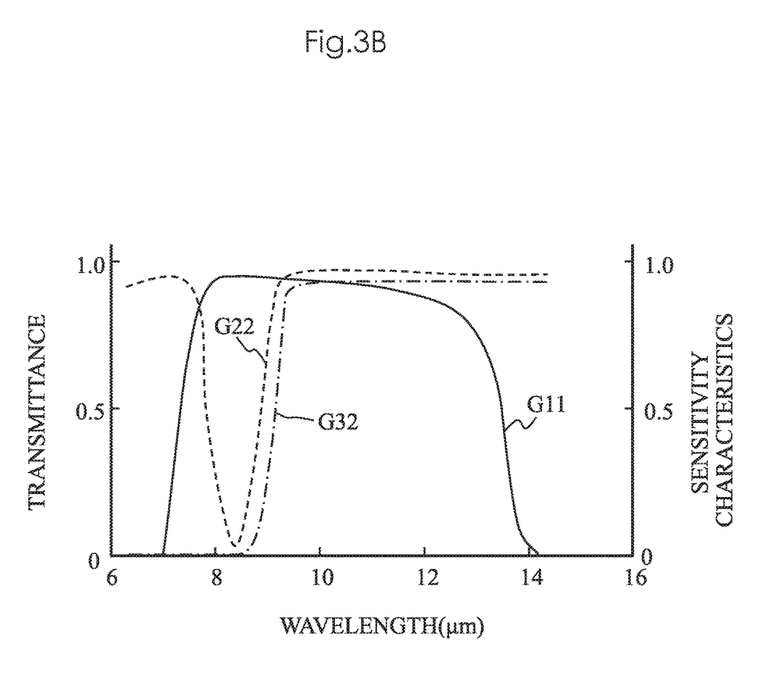
FIG. 3B is a graph showing spectroscopic transmittance characteristics of a detection target object, spectroscopic transmittance characteristics of a filter, and spectroscopic sensitivity characteristics of an image sensor.
Figure 3C:
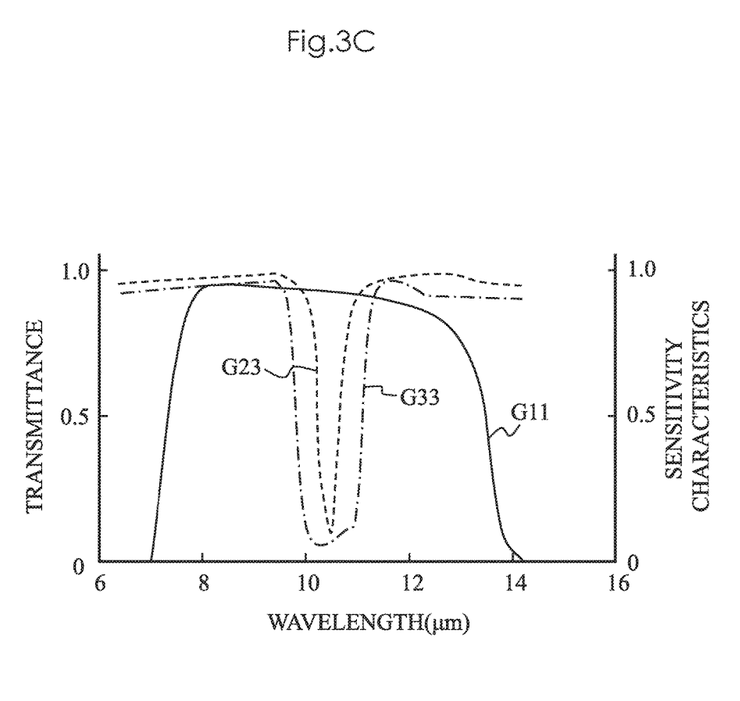
FIG. 3C is a graph showing spectroscopic transmittance characteristics of a detection target object, spectroscopic transmittance characteristics of a filter, and spectroscopic sensitivity characteristics of an image sensor.

The filter 30 is an optical filter that cuts light in the wavelength range that the detection target object absorbs. FIGS. 3A to 3C are graphs showing the spectroscopic transmittance characteristics of the filter and the spectroscopic sensitivity characteristics of the image sensor. In FIGS. 3A to 3C, the first vertical axis represents transmittance, the second vertical axis represents sensitivity characteristics, and the horizontal axis represents wavelength. The solid lines indicate the curve G11 of the sensitivity characteristics of the image sensor 20. The broken lines indicate the curves G21, G22, and G23 of the spectroscopic transmittance characteristics of different detection target objects respectively. The dash-and-dot lines indicate the curves G31, G32, and G33 of the spectroscopic transmittance characteristics of corresponding filters 30 respectively.

Based on the wavelength range that the detection target object absorbs and the wavelength range in which the image sensor 20 has high sensitivity, the transmittance characteristics of the filter 30 are determined. As shown in FIG. 3A, with a detection target object G21 of which the absorption wavelength lies near the upper limit of the sensitivity wavelength range of the image sensor 20, a high-eat filter G31 that transmits light on the shorter side of the absorption wavelength is adopted. As shown in FIG. 3B, with a detection target object G22 of which the absorption wavelength lies near the lower limit of the sensitivity wavelength range of the image sensor 20, a low-cut filter G32 that transmits light on the higher side of the absorption wavelength is adopted. As shown in FIG. 3C, with a detection target object G23 of which the absorption wavelength lies near the middle of the sensitivity wavelength range of the image sensor 20, a band-cut filter G33 that transmits light on the shorter and longer sides of the absorption wavelength is adopted.

The wavelengths that the filter 30 transmits (the wavelengths that it cuts) can be changed by changing its material. For example, in a case where the absorption wavelength lies in a wavelength range spanning from the visible to near-infrared regions, an optical glass or the like is used; in a case where the absorption wavelength lies in a wavelength range spanning from the mid-infrared to far-infrared regions, Ge, Si, chalcogenide glass, or the like is used. When used, these infrared light transmitting materials have their surface coated with a thin film for adjusting the spectroscopic transmittance.

The connection interface 50 is an interface for connecting the optical detection device A to an external device. Examples of the connection interface 50 include terminals for wired connection, such as a USB cable or an optical cable. It may instead be an interface (antenna) for wireless communication, such as a wireless LAN or Bluetooth (a registered trademark).

The processor 60 controls the operation of the imaging optical system 10, the image sensor 20, and the filter driver 40. The processor 60 also serves as a processor for correcting shot image data acquired by the image sensor 20 and for acquiring, based on the shot image data, the presence or absence of a detection target object and its position, density, and the like. The processor 60 includes a operational processing circuit such as an MPU or a CPU. The processor 60 also includes, or is connected to, a storage (memory), though omitted from illustration. In the memory, data is stored temporarily during operational processing, and also programs for processing are stored.

The imaging optical system 10, the image sensor 20, the filter 30, the filter driver 40, the connection interface 50, and the processor 60 are arranged inside the housing 70. Part of the connection interface 50 is exposed outside the housing 70 for connection with a cable. For protection of the components from foreign matter such as moisture, dust, and dirt, the housing 70 is configured to be hermetically sealed against entry of foreign matter such as moisture, dust, and dirt; it is also configured to have such mechanical strength as to withstand impacts and vibrations from outside.

The optical detection device A according to the present invention is configured as described above. The optical detection device A is employed to detect gaseous substances in a laboratory, or in a manufacturing room (for example, a clean room) where articles are manufactured, and is thus so set up as to capture black body radiation light from a detection region at a constant angle of view all the time. Thus, the optical detection device A as a whole including the housing 70 is kept stationary.

Next, the operation of the optical detection device A according to the present invention will be described. In the optical detection device A according to the present invention, an uncooled sensor is used as the image sensor 20. In an uncooled sensor, a plurality of pixels each have a fine three-dimensional structure; their shape is prone to variations ascribable to the manufacturing process, and those variations manifest themselves as variations in shot data. Moreover, an uncooled sensor is also influenced by the heat (infrared light) resulting from its own driving and other ambient heat (infrared light).

With that taken into consideration, in a case where an uncooled sensor is used as the image sensor 20, pixel characteristics correction is performed on the image sensor 20 to increase the accuracy of the shot image. Pixel characteristics correction is achieved through gain characteristics correction.

Next, gain characteristics correction will be described. The image sensor 20 receives infrared light, and converts the infrared light into an electric signal. The photoelectric element that constitutes each pixel converts light into an electric current, and has such characteristics that, the larger the amount of light it receives, it produces the higher electric, current by conversion. In the image sensor 20, which is an uncooled sensor, variations also occurs, among pixels, in the gradient (constant or proportion, gain) which is the ratio of the change of the amount of light received to the change of the electric current. Thus, in the optical detection device A according to the present invention, correction is performed to correct the gradient, which reflects the gain characteristics, on a pixel-to-pixel basis.

Figure 4:
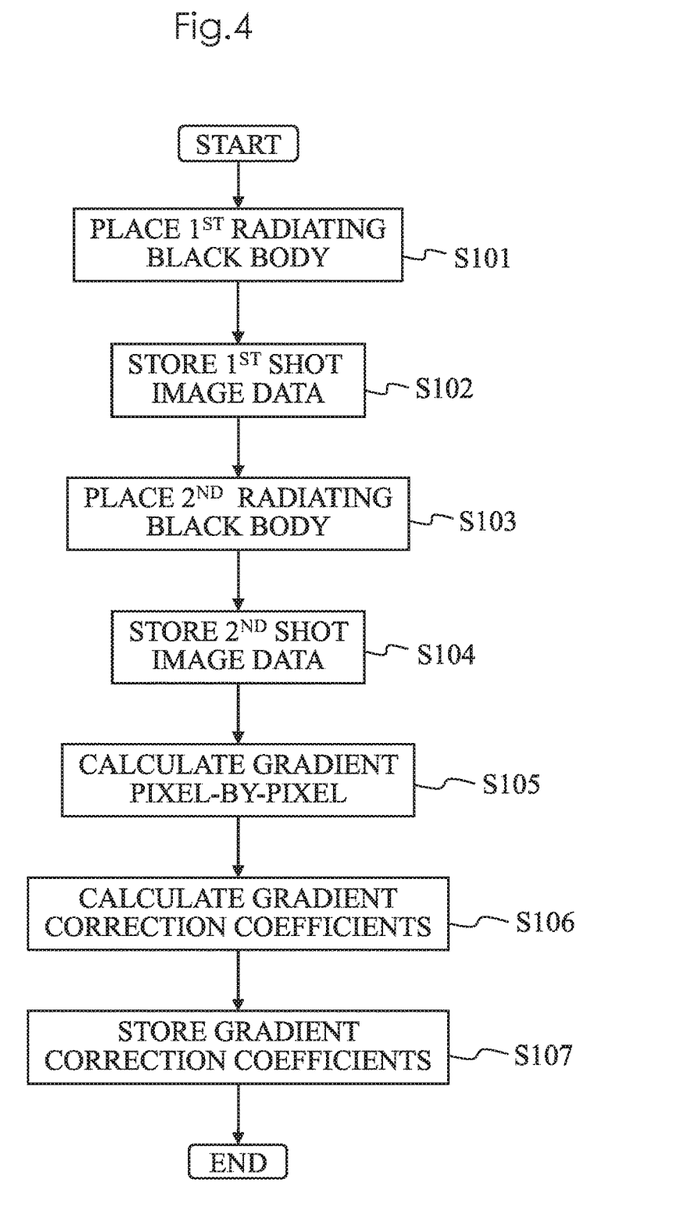
FIG. 4 is a flow chart of gain characteristics correction in an optical detection device according to the present invention.

FIG. 4 is a flow chart of gain characteristics correction in an optical detection device according to the present invention. The gain characteristics correction is performed once during the manufacture of the optical detection device A, and the corrected gradient values (gain values) are stored in the storage in the processor 60.

When the gain characteristics correction is performed, a first radiating black body with a first radiation intensity is placed in front of the image sensor 20 (step S101). Then, first shot data obtained by shooting the first radiating black body with the image sensor 20 is stored (step S102). The first radiating black body is then put away, and a second radiating black body with a second radiation intensity is placed in front of the image sensor 20 (step S103). Then, shot data obtained by shooting the second radiating black body with the image sensor 20 is stored (step S104).

For each pixel, the gradient (gain) is calculated from the first radiation intensity, the second radiation intensity, the first shot data, and the second shot data (step S105). Then, the gradients at all the pixels are compared together and the gain correction coefficient for each pixel is calculated such that the gradients at all the pixels are equal (step S106). Then, the gradient correction coefficients are stored in the storage in the processor 60 (step S107).

With the gradient correction coefficients described above, the change of pixel data against the change of the amount of light received can be made uniform over all the pixels of the image sensor 20.

Figure 5:
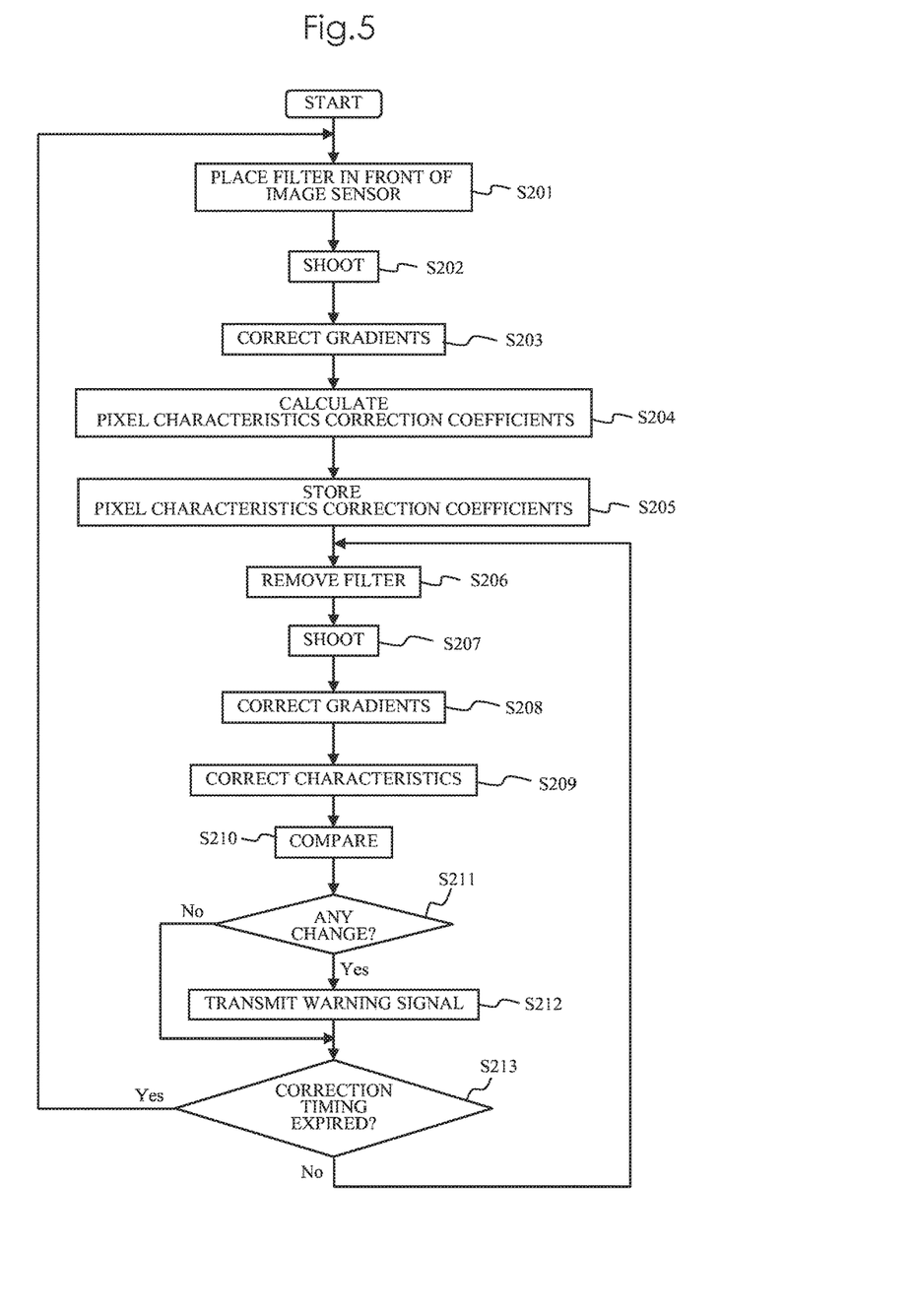
FIG. 5 is a flow chart of a procedure for detecting a detection target object in a detection region as performed by an optical detection device according to the present invention.

The operation of the optical detection device A according to the present invention will now be described. FIG. 5 is a flow chart of a procedure for detecting a detection target object in a detection region as performed by an optical detection device according to the present invention. First, the processor 60 drives the filter driver 40 to place the filter 30 in front of the image sensor 20 (step S201). Then, black body radiation light from the detection region is shot with the image sensor 20 through the filter 30 (step S202). As described previously, the filter 30 cuts the absorption wavelength range of the detection target object, and thus by the shooting of black body radiation light from the detection region through the filter 30, it is possible to acquire image data free from influence of the absorption wave range of the detection target object.

The image sensor 20 has pixel-to-pixel variations, and the image data includes influence of the pixel-to-pixel variations. That is, the image data shot through the filter 30 includes influence of the pixel-to-pixel variations but no influence of the absorption wavelength range of the detection target object. The processor 60 corrects the image data with the previously stored gradient correction coefficients (step S203).

For correction to image data estimated values shot without the filter 30 as estimated from the image data, pixel-to-pixel pixel characteristics correction coefficients η are calculated (step S204). Almost all substances (solid or liquid) are supposed to have an approximately uniform emissivity over the observation wavelengths, and thus from an emissivity in a partial wavelength range, an emissivity in a wider wavelength range can be calculated. Then, based on the pixel-to-pixel pixel characteristics correction coefficients η, the processor 60 corrects the image data to obtain image data estimated values (step S205). These pixel-to-pixel pixel characteristics correction coefficients η are calculated according to Expression 1 below when the spectroscopic transmittance characteristics of the filter are represented by $T(\lambda)$, the sensitivity wavelength range of the image sensor 20 is represented by $\lambda 1-\lambda 2$, and its spectroscopic sensitivity characteristics are represented by $S(\lambda)$.

$$\eta = \int_{\lambda_2}^{\lambda_3} S(\lambda) d\lambda / \int_{\lambda_2}^{\lambda_3} T(\lambda) S(\lambda) d\lambda \qquad \text{[Expression 1]}$$

Compared with planar-direction variations in pixel characteristics, relative spectroscopic sensitivity variations in pixel characteristics are far smaller. Thus, pixel-to-pixel variations in the above-mentioned pixel characteristics correction coefficients can be ignored. The spectroscopic sensitivity characteristics $S(\lambda)$ generally depend on the ambient temperature, but only the proportion of electrical output signal amount to the incident energy varies, and the relative spectroscopic sensitivity hardly varies. Also with the filter 30, the transmittance hardly varies in magnitude in relative terms among different wavelengths against the ambient temperature. Thus, the pixel characteristics correction coefficients η hardly depend on the ambient temperature. Therefore, the pixel characteristics correction coefficients η can be measured and stored in the device before factory shipment.

Examples of the pixel characteristics correction coefficients η will be described below with reference to the relevant drawings. First, an example of the pixel characteristics correction coefficients η when, as the filter 30, one with high-cut characteristics is used will be presented. Specifically, when the image sensor 20 and the filter 30 shown in FIG. 3A are used, the pixel characteristics correction coefficients η are given as noted below. Here, the sensitivity wavelength range is $\lambda 1$ (7 μm)-$\lambda 2$ (14 μm).

$$\int_{\lambda_2}^{\lambda_3} S(\lambda) d\lambda = 5.596$$

$$\int_{\lambda_2}^{\lambda_3} T(\lambda) S(\lambda) d\lambda = 3.443$$

$$\eta = 1.625 \qquad \text{[Expression 2]}$$

Next, an example of the pixel characteristics correction coefficients η when, as the filter 30, one with low-cut characteristics is used will be presented. Specifically, when the image sensor 20 and the filter 30 shown in FIG. 3B are used, the pixel characteristics correction coefficients η are given as noted below. Here, the sensitivity wavelength range is $\lambda 1$ (7 μm)-$\lambda 2$ (14 μm).

$$\int_{\lambda_2}^{\lambda_3} S(\lambda) d\lambda = 5.596$$

$$\int_{\lambda_2}^{\lambda_3} T(\lambda) S(\lambda) d\lambda = 3.836$$

$$\eta = 1.458 \qquad \text{[Expression 3]}$$

Presented above are merely examples of the pixel characteristics correction coefficients η, which are not meant as any limitation. As described above, the pixel characteristics correction coefficients η vary with the spectroscopic sensitivity characteristics of the image sensor 20 and the spectroscopic transmittance characteristics of the filter 30.

The processor 60 instructs the filter driver 40 to remove the filter 30 from in front of the image sensor 20 (step S206). Then, black body radiation light from the detection region is shot with the image sensor 20 (step S207). The processor 60 corrects, with the gradient correction coefficients previously stored for the shot data from the image sensor 20, the shot data to obtain shot data (step S208).

The processor 60 compares the image data estimated values obtained at step S205 with the shot data obtained at step S208 (step S210). It is checked whether or not the shot data includes any pixel of which the data differs from the image data estimated value by a predetermined value or more (step S211). For example, the difference between the data of each pixel in the image data estimated value and the data of each pixel in the shot data is calculated to check for any pixel of which the difference exceeds a threshold value.

If the shot data includes any pixel of which the data differs from the image data estimated value by a predetermined value or more (step S211, Yes), then the processor 60 judges that the detection region includes a detection target object (for example, a gas is leaking), and transmits a warning signal from the connection interface 50 (Step S212). By contrast, if the shot data includes no pixel of which the data differs from the image data estimated value by a predetermined value or more (step S211, No), then the processor 60 judges that the detection region includes no detection target object.

Then, it is checked whether or not timing for correction has expired (step S213). If timing for correction has not expired (step S213, No), black body radiation light from the detection region is shot with the image sensor 20 without the filter 30 (a return is made to step S207). If timing for correction has expired (step S213, Yes), black body radiation light from the detection region is shot with the image sensor 20 through the filter 30 (a return is made to step S201).

Here, timing for correction will be explained. The temperature in the detection region changes from moment to moment with change in the ambient temperature and change in solar irradiation; thus, observing the same scene yields varying shot data. For this reason, in a time zone when the ambience changes greatly, as during the day on a sunny day, it is preferable to perform shooting through the filter 30 immediately before the shooting without the filter 30 that is performed to detect a detection target object. On the other hand, in a time zone when the ambience hardly changes, as at night, the two types of shooting can be performed at an interval.

As described above, by use of the optical detection device A, it is possible, by using the image sensor 20, which is an uncooled sensor, to detect the presence or absence of a detection target object in a detection region while performing pixel characteristics correction on the image sensor 20. This makes it possible to omit a radiating black body and a driving mechanism for pixel characteristics correction; it is thus possible to achieve a simple structure and compact size, and to reduce the number of movable components and thereby diminish the occurrence of failure, contributing to a longer life time. The reduced number of movable components makes maintenance and repair easy.

In this embodiment, from the spectroscopic sensitivity characteristics of the image sensor 20 and the spectroscopic transmittance characteristics of the filter 30, the pixel characteristics correction coefficients η are calculated. Then, from the image data shot through the filter 30 and the pixel characteristics correction coefficients η, image data estimated values as estimated if shot without the filter 30 are acquired. Thereafter, image data shot without the filter 30 is acquired. The shot data and the image data estimated values are compared to detect the presence or absence of a detection target object within the detection region. This, however, is not meant as any limitation.

For example, the pixel characteristics correction coefficients η may be so determined as to make image data identical with the image data previously provided in the processor. Then, a shot data is corrected with the pixel characteristics correction coefficients η, and is then compared with the previously provided image data so that, if any part differs by a predetermined value or more, it can be judged that a detection target object is present. For another example, in a shot image shot with the filter 30 removed, the change of image data and its magnitude can be compared minutely to detect, to a certain degree, the distribution and density of the detection target object.

The optical detection device A according to the present invention is configured to shoot black body radiation light from a detection region and judge whether a detection target object is present or absent in the detection region. Thus, it is possible to detect from a remote position a detection target object which is a toxic, flammable, or otherwise hazardous substance, and thus to detect it safely.

The optical detection device described above assumes that a detection target object absorbs light in a predetermined wavelength range; however, it is also possible to detect in a similar manner one that emits light in a predetermined wavelength range under certain conditions. In a configuration for emitted light to eliminate the influence of the emitted, light, the fitter can be configured to cut the wavelength range of the emitted light.

EXAMPLE 1

Some practical examples employing an optical detection device according to the present invention will be presented below. A description will now be given of a case where an optical detection device according to the present invention is used to build a detection device that detects ethane gas. Ethane gas has an absorption wavelength around 11.2 μm to 13.2 μm. Accordingly, as the image sensor 20, a microbolometer with a sensitivity wavelength range of 7 μm to 14 μm was used. The absorption wavelength of ethane gas lies near the upper limit of the sensitivity wavelength range of the image sensor 20, and thus, as the filter 30, a filter (high-cut filter) that transmits light in a wavelength range shorter than 11 μm was used (see FIG. 3A).

A description will now be given of a ease where an optical detection device according to the present invention is used to build a detection device that detects methane gas. Methane gas has an absorption wavelength around 7.0 μm to 8.2 μm. Accordingly, as the image sensor 20, a microbolometer with a sensitivity wavelength range of 7 μm to 14 μm was used. The absorption wavelength of methane gas lies near the lower limit of the sensitivity wavelength range of the image sensor 20, and thus, as the filter 30, a filter (low-cut filter) that transmits light in a wavelength range longer than 8.5 μm was used (see FIG. 3B).

A description will new be given of a case where an optical detection device according to the present invention is used to build a detection device that detects methanol vapor. Methanol vapor has an absorption wavelength around 9.3 μm to 10.5 μm. Accordingly, as the image sensor 20, a microbolometer with a sensitivity wavelength range of 7 μm to 14 μm was used. The absorption wavelength of methanol vapor lies near a middle part of the sensitivity wavelength range of the image sensor 20, and thus, as the filter 30, a filter (band-cut filter) that transmits light in a wavelength range longer than 7 μm to 9 μm and 11 μm was used (see FIG. 3C).

The embodiments by way of which the present invention is described above are not meant to limit how the invention should be implemented. The embodiments of the present invention allow for many modifications without departing from the spirit of the invention.

LIST OF REFERENCE SIGNS

A optical detection device
10 imaging optical system
20 image sensor
30 filter
40 filter driver
50 connection interface
60 processor
70 housing

The invention claimed is:

1. An optical detection device, comprising:
    an uncooled image sensor that has a plurality of pixels that convert light from a detection region into electricity;
    a filter that eliminates light in a wavelength range that is influenced by the detection target object;
    a filter driver that places or removes the filter in front of or from in front of the image sensor; and
    a processor that detects presence or absence of the detection target by processing data from the image sensor, wherein the processor determines a correction coefficient by which image data that is obtained by shooting through the filter is corrected to image data estimated values that are estimated to be obtained by shooting without the filter, and the processor determines the presence or absence of the detection target object by comparing the image data estimated values that are obtained by correction using the correction coefficient from the image data with shot data that is obtained by shooting the detection region with the filter removed from in front of the image sensor.

2. The optical detection device of claim 1, wherein the processor determines a gradient correction coefficient by which a rate of change of output to change of intensity of pixel-to-pixel incoming light is corrected to a previously given standard rate of change, to correct the image data.

3. The optical detection device of claim 2, wherein the correction is repeated at a predetermined interval.

4. The optical detection device of claim 3, wherein a wavelength range that is eliminated by the filter includes a wavelength range absorbed by the detection target object.

5. The optical detection device of claim 4, wherein the detection target object is a gaseous object.

6. The optical detection device of claim 3, wherein a wavelength range that is eliminated by the filter includes a wavelength range emitted by the detection target object.

7. The optical detection device of claim 6, wherein the detection target object is a gaseous object.

8. The optical detection device of claim 3, wherein the detection target object is a gaseous object.

9. The optical detection device of claim 2, wherein a wavelength range that is eliminated by the filter includes a wavelength range absorbed by the detection target object.

10. The optical detection device of claim 9, wherein the detection target object is a gaseous object.

11. The optical detection device of claim 2, wherein a wavelength range that is eliminated by the filter includes a wavelength range emitted by the detection target object.

12. The optical detection device of claim 11, wherein the detection target object is a gaseous object.

13. The optical detection device of claim 2, wherein the detection target object is a gaseous object.

14. The optical detection device of claim 1, wherein the correction is repeated at a predetermined interval.

15. The optical detection device of claim 14, wherein the detection target object is a gaseous object.

16. The optical detection device of claim 1, wherein a wavelength range that is eliminated by the filter includes a wavelength range absorbed by the detection target object.

17. The optical detection device of claim 16, wherein the detection target object is a gaseous object.

18. The optical detection device of claim 1, wherein a wavelength range that is eliminated by the filter includes a wavelength range emitted by the detection target object.

19. The optical detection device of claim 18, wherein the detection target object is a gaseous object.

20. The optical detection device of claim 1, wherein the detection target object is a gaseous object.

* * * * *